United States Patent [19]

Davatz et al.

[11] Patent Number: 4,642,350
[45] Date of Patent: Feb. 10, 1987

[54] NOVEL PROCESS FOR PREPARATION OF BENZOTRIAZOLES USING ARYLDIOLS AND QUINONES

[75] Inventors: Alexander Davatz, Bubendorf; Tibor Somlo, Birsfelden, both of Switzerland

[73] Assignee: Ciba-Geigy Corporation, Ardsley, N.Y.

[21] Appl. No.: 810,544

[22] Filed: Dec. 18, 1985

Related U.S. Application Data

[63] Continuation of Ser. No. 616,322, May 31, 1984, abandoned.

[30] Foreign Application Priority Data

Jun. 1, 1983 [CH] Switzerland ............... 2986/83

[51] Int. Cl.⁴ .......................................... C07D 249/20
[52] U.S. Cl. ................................. 548/260; 548/257
[58] Field of Search ............................. 548/260, 257

[56] References Cited

U.S. PATENT DOCUMENTS

| | | | |
|---|---|---|---|
| 3,076,782 | 2/1963 | Mohr et al. | 548/260 |
| 4,048,157 | 9/1977 | Cooper et al. | 548/519 |
| 4,122,092 | 10/1978 | Kende et al. | 549/447 |
| 4,220,788 | 9/1980 | Bader et al. | 548/259 |

FOREIGN PATENT DOCUMENTS

| | | | |
|---|---|---|---|
| 1073463 | 11/1980 | Canada | 548/260 |
| 2455155 | 5/1975 | Fed. Rep. of Germany | 548/260 |
| 2551853 | 5/1976 | Fed. Rep. of Germany | 548/260 |
| 3063379 | 6/1978 | Japan | 548/260 |

OTHER PUBLICATIONS

Hashimoto, et al., "... Catalytic Effects of Quinones on Sodium Disulfide Reduction of Azobenzene," Chem. Abst. 66:64836(X) (1967).
Chem. Abst. 98, 126102b (1983).
Chem. Abst. 102, 113511k (1985).
Chem. Abst. 102, 45959k (1985).
Organikum (Practical Organic Chemistry) Berlin 1976, p. 604.

Primary Examiner—Glenna M. Hendricks
Attorney, Agent, or Firm—Luther A. R. Hall

[57] ABSTRACT

Process for preparing 2-(2'-hydroxyphenyl)-benzotriazoles of the formula

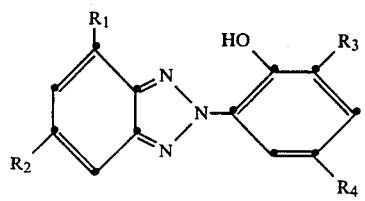

from 2-nitro-2'-hydroxyazobenzenes of the formula

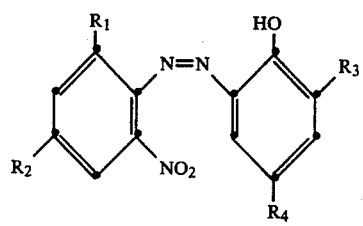

which comprises reducing a 2-nitro-2'-hydroxyazobenzene compound in a strongly basic medium in the presence of an aromatic dihydroxy or dioxo compound as catalyst and of an alcohol having more than one carbon atom. The 2-(2'-hydroxyphenyl)-benzotriazole compounds are known stabilizers for organic materials.

8 Claims, No Drawings

NOVEL PROCESS FOR PREPARATION OF BENZOTRIAZOLES USING ARYLDIOLS AND QUINONES

This application is a continuation of application Ser. No. 616,322, filed May 31, 1984, now abandoned.

The present invention relates to a process for preparing 2-(2'-hydroxyphenyl)-benzotriazoles from 2-nitro-2'-hydroxyazobenzenes.

The reduction of 2-nitro-2'-hydroxyazobenzenes to 2-(2'-hydroxyphenyl)-benzotriazoles in a basic alcoholic medium is known. In addition to an aromatic dihydroxy or dioxo compound being present as the catalyst, this reduction however also requires the presence of reducing agents such as zinc, ammonium sulfide, alkali metal sulfide, ammonium hydrogensulfide, alkali metal hydrogensulfide, alkali metal dithionite or hydrazine hydrate (Japanese Patent Application No. 63379/78). And it is technically complicated to remove the oxides produced on reducing with metals such as zinc and furthermore to prevent these oxides from polluting the waste water. The sulfur-containing reducing agents are inferior to the metals and leave behind in the products sulfur impurities which are difficult to remove. Hydrazine hydrate is admittedly a powerful reducing agent, but because of its high toxicity its handling constitutes a safety risk.

In the processes for reducing 2-nitro-2'-hydroxyazobenzenes to 2-(2'-hydroxyphenyl)-benzotriazoles which have been described to date, alcohols, so far as they were used at all, served as solvents. Moreover, to date it has been the general experience that nitro groups are not attacked by basic alcohol solutions (see ORGANIKUM [Practical Organic Chemistry], published by VEB Deutscher Verlag der Wissenschaften, Berlin 1976, page 604). The search for a more economical and environmentally more acceptable process has now led to the discovery of reaction conditions by which 2-nitro-2'-hydroxyazobenzenes can after all be reduced with basic alcohol solutions whose alcohol has more than one carbon atom to form 2-(2'-hydroxyphenyl)-benzotriazoles.

The present invention accordingly provides a process for preparing 2-(2'-hydroxyphenyl)-benzotriazoles from 2-nitro-2'-hydroxyazobenzenes, which comprises reducing a 2-nitro-2'-hydroxyazobenzene compound in a strongly basic medium in the presence of an aromatic dihydroxy or dioxo compound as catalyst and of an alcohol having more than one carbon atom.

The process according to the invention is preferably used for preparing, from compounds of the formula II, compounds of the formula I

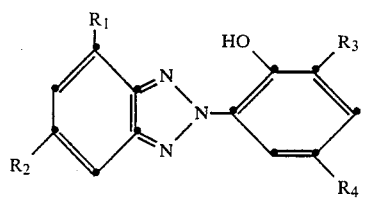

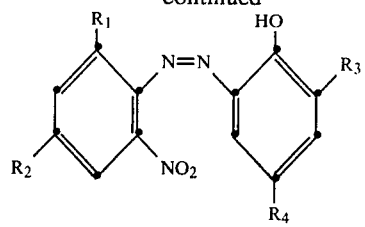

in which $R_1$ is hydrogen or halogen, $R_2$ is hydrogen, alkyl, alkoxy or halogen, $R_3$ is hydrogen, alkyl, cycloalkyl, aralkyl or aryl, and $R_4$ is hydrogen, alkyl, cycloalkyl, aralkyl, aryl or alkoxy.

In earlier processes the alcohol, so far as it was used at all, only had a solvent function. It always had to be added in addition to a reducing agent. In the process according to the invention, by contrast, the alcohol has a twofold function, acting as solvent and reducing agent. This does away with one raw material, compared with the earlier processes. Since, moreover, no reducing agents such as zinc, sulfide, hydrogensulfide, dithionite or hydrazine hydrate are required any longer, the abovementioned disadvantages concerning work load and environmental and safety aspects also disappear. There is no longer a need for the laborious separating processes required in particular in the case of metallic reducing agents. At the end of the process the reaction product is precipitated in each case and is readily isolated. The yields are high. The novel process is thus more economical and environmentally more acceptable.

The process according to the invention is particularly preferably used for preparing, from compounds of the formula II, compounds of the formula I in which $R_1$ is hydrogen or chlorine, $R_2$ is hydrogen, alkyl having 1 to 5 carbon atoms, alkoxy having 1 to 4 carbon atoms or chlorine, $R_3$ is hydrogen, alkyl having 1 to 12 carbon atoms, cycloalkyl having 5 to 8 carbon atoms, aralkyl having 7 to 9 carbon atoms or phenyl, and $R_4$ is hydrogen, alkyl having 1 to 12 carbon atoms, cycloalkyl having 5 to 8 carbon atoms, aralkyl having 7 to 9 carbon atoms, phenyl or alkoxy having 1 to 12 carbon atoms.

Halogen $R_1$ and $R_2$ can be chlorine. Alkyl $R_2$ can be for example methyl, ethyl, propyl, isopropyl, n-butyl, tert.-butyl, amyl or tert.-amyl. Alkoxy $R_2$ can be for example methoxy, ethoxy or n-butoxy. Alkyl $R_3$ and $R_4$ can be for example methyl, ethyl, sec.-butyl, tert.-butyl, tert.-amyl, tert.-octyl or n-dodecyl. Cycloalkyl $R_3$ and $R_4$ can be for example cyclopentyl, cyclohexyl or cyclooctyl. Aralkyl $R_3$ and $R_4$ can be for example benzyl, α-methylbenzyl or α,α-dimethylbenzyl. Aryl $R_3$ and $R_4$ can be phenyl. Alkoxy $R_4$ can be for example methoxy, ethoxy, propoxy, butoxy, pentyloxy, isobutoxy, octyloxy or dodecyloxy.

Typical compounds of the formula I are prepared in the examples.

Suitable alcohols for the process according to the invention have more than one carbon atom. The upper limit of the number of carbon atoms is governed by the requirement that the alcohol used must still be liquid at room temperature. The alcohol can be in particular a primary alkanol, a secondary alkanol, an aralkanol, a glycol or a glycol monoalkyl ether. Examples of preferred primary alkanols are ethanol, n-propanol, n-butanol, n-octyl alcohol and n-dodecanol. Examples of preferred secondary alkanols are isopropanol, sec.- butanol, sec.-octanol and sec.-dodecanol. An example of a preferred aralkanol is benzyl alcohol. Examples of preferred glycols are 1,2-ethanediol, 1,3-propanediol and 1,4-butanediol. Examples of preferred glycol monoalkyl ethers are ethylene glycol monomethyl ether, ethylene glycol monoethyl ether and ethylene glycol monobutyl ether. Secondary alkanols are particularly preferable. Isopropanol and sec.-butanol are very particularly preferable.

The strongly basic medium in the process according to the invention can be produced by adding an alkali metal hydroxide such as sodium hydroxide or potassium hydroxide, preferably sodium hydroxide, or an alkali metal such as sodium or potassium, preferably sodium, to one of the alcohols defined above. Said alkali metal hydroxides and alkali metals can be used in at least one preferably two mole equivalents relative to the substrate to be reduced.

The function of catalyst in the process according to the invention is performed by aromatic dihydroxy or aromatic dioxo compounds.

Aromatic dihydroxy compounds can be benzodiols, for example 1,2-benzodiols and 1,4-benzodiols, or naphthodiols, for example 1,2-naphthodiols, 1,4-naphthodiols and 2,6-naphthodiols. The aromatic nuclei can be unsubstituted or be completely or partially substituted by alkyl or halogen. Unsubstituted benzodiols are preferred.

Aromatic dioxo compounds can be benzoquinones or naphthoquinones. The benzoquinones can be unsubstituted or completely or partially alkyl-, such as methyl-, or halogen-, such as chlorine-, substituted 1,2-benzoquinones and 1,4-benzoquinones. The benzoquinones take second preference to unsubstituted or substituted naphthoquinones, such as 1,2-naphthoquinones, 1,4-naphthoquinones or 2,6-naphthoquinones. Substituted nuclei are substituted by halogen, hydroxyl, alkyl, dialkylamino, piperidino or morpholino. Preferred 1,4-naphthoquinones have the formula III

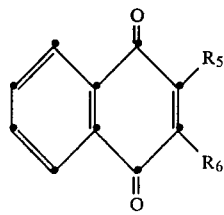

III in which $R_5$ is hydrogen, halogen or hydroxyl, and $R_6$ is hydrogen, halogen, alkyl, dialkylamino, piperidino or morpholino.

Particularly preferred compounds have the formula III in which $R_5$ is hydrogen, chlorine or hydroxyl, and $R_6$ is hydrogen, chlorine, alkyl having 1 to 12 carbon atoms, dialkylamino having 2 to 24 carbon atoms, piperidino or morpholino.

Alkyl $R_6$ can be for example methyl, ethyl, n-butyl, sec.-butyl, n-octyl or n-dodecyl. Dialkylamino $R_6$ can be dimethylamino, diethylamino, dibutylamino, dioctylamino or didodecylamino.

The process according to the invention is very particularly preferably carried out with 1,4-naphthoquinone, 2,3-dichloronaphthoquinone, 2-chloronaphthoquinone, 2-hydroxy-3-methylnaphthoquinone or 2-chloro-3-dimethylaminonaphthoquinone.

The aromatic dihydroxy or dioxo compounds acting as the catalyst can be used, for example, in amounts of 1-20 mole %, in particular 5-10 mole %, relative to the substrate to be reduced.

The process according to the invention is preferably carried out with a cocatalyst being used in addition to the catalyst. Suitable cocatalysts are alkali metal bisulfites and ammonium bisulfite. Sodium bisulfite used in amounts of, for example, 1-20 mole %, in particular 5-10 mole %, relative to the substrate to be reduced is preferred.

The process according to the invention can be carried out at about 20° C. to about 120° C., in particular at about 40° C. to about 100° C., and especially at about 50° C. to about 80° C.

In the process according to the invention, the water content of the reaction medium should be less than 15% by volume. The reduction is preferably carried out in an anhydrous medium.

The compounds of the formula I are known stabilisers for organic materials, for example organic polymers. The compounds of the formula II are known for use as starting materials.

The following examples describe the invention in more detail.

EXAMPLE 1

A 750 ml sulfonating flask is charged with 200 g of isopropanol, 1 g of sodium bisulfite and 2.3 g of 2,3-dichloronaphthoquinone. The mixture is refluxed for an hour and is then cooled down to 60° C., when 25.6 g of sodium hydroxide and 38.35 g of 2-nitro-2'-hydroxy-3',5'-bis-tert.-amylazobenzene are added. The mixture is stirred at 70°-75° C. for one to two hours, and 500 ml of water are then added. The precipitated crystals are filtered off, are washed with water and dried at 60°-70° C. in vacuo. The product is a high yield of 2,4-di-tert.-amyl-6-(2'-benzotriazolyl)-phenol.

EXAMPLE 2

A suspension of 9.2 g of sodium in 400 g of isopropanol is refluxed in a 1.5 liter sulfonating flask until a solution is formed. To this are added, at 60° C., 3.2 g of 1,4-naphthoquinone, 2.1 g of sodium bisulfite and 71 g of 2-nitro-2'-hydroxy-3',5'-bis-tert.-butylazobenzene. The mixture is stirred at 60° C. for between half an hour and a full hour. 20 g of 17 percent by volume aqueous sulfuric acid and 100 ml of warm water at 60°-70° C. are then added dropwise. The precipitated crystals are filtered and are washed with warm 60 percent by weight aqueous methanol and with warm water. Drying at 70°-80° C. n vacuo produces 2,4-di-tert.-butyl-6-(2'-benzotriazolyl)-phenol in a high yield.

EXAMPLE 3

A 750 ml sulfonating flask is charged with 220 g of sec.-butanol, 34.7 g of 2-nitro-4-chloro-2'-hydroxy-3'-tert.-butyl-5-methylazobenzene, 2.3 g of 2,3-dichloronaphthoquinone and 26 g of 50 percent by weight aqueous sodium hydroxide solution. The mixture is stirred at 40°-45° C. for two hours and at 70°-75° C. for three hours. 500 ml of water are added dropwise. The precipitated crystals are filtered off, are washed with water, and are dried at 60°-70° C. in vacuo. The product is a high yield of 2-tert.-butyl-4-methyl-6-(4'-chloro-2'-benzotriazolyl)-phenol.

EXAMPLE 4

A 750 ml sulfonating flask is charged with 300 g of cyclohexanol, 35.5 g of 2-nitro-2'-hydroxy-3',5'-bis-tert.-butylazobenzene, 2.3 g of 2,3-dichloronaphthoquinone and 25.6 g of sodium hydroxide. The mixture is stirred at 70°–75° C. for three hours and is brought to pH 1.5 with 5 percent by volume aqueous hydrochloric acid. The aqueous phase is separated off and discarded. The organic phase is washed with water and cooled down to −5° C. A high yield of 2,4-di-tert.-butyl-6-(2'-benzotriazolyl)-phenol crystallises out.

EXAMPLE 5

200 g of isopropanol are heated to 60° C. in a 750 ml sulfonating flask, and 1 g of sodium bisulfite, 1.6 g of 1,4-naphthoquinone, 14 g of sodium hydroxide and 35.5 g of 2-nitro-2'-hydroxy-3',5'-bis-tert.-butylazobenzene are then added. The mixture is stirred at 75°–80° C. for two hours, and 18 g of 17 percent by volume aqueous sulfuric acid and 50 ml of warm water are then added dropwise. The precipitated crystals are washed with warm methanol and then with warm water. The product is a high yield of 2,4-di-tert.-butyl-6-(2'-benzotriazolyl)-phenol.

What is claimed is:

1. A process for preparing a 2-(2-hydroxyphenyl)-2H-benzotriazole from the corresponding 2-nitro-2'-hydroxyazobenzene, which consists essentially of reducing said 2-nitro-2'-hydroxyazobenzene in the presence of a strongly basic medium and in the presence of an alcohol having more than one carbon atom and of a catalyst selected from the group consisting of the benzodiols, the naphthodiols, said benzodiols or said naphthodiols substituted by alkyl or by halogen, the benzoquinones, said benzoquinones substituted by alkyl or by halogen, the naphthoquinones and said naphthoquinones substituted by halogen, by hydroxyl, by alkyl, by dialkylamino, by piperidino or by morpholino; at a temperature of 20° C. to 120° C.

2. A process according to claim 1, wherein there are prepared, from a compound of the formula II, a compound of the formula I

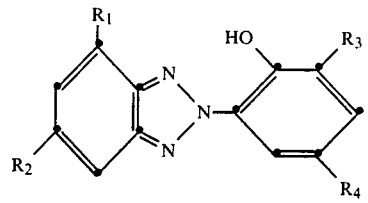

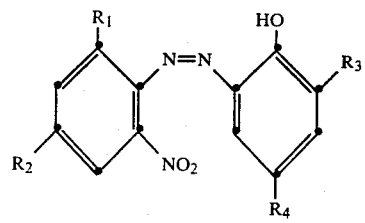

in which $R_1$ is hydrogen or halogen, $R_2$ is hydrogen, alkyl, alkoxy or halogen, $R_3$ is hydrogen, alkyl, cycloalkyl, aralkyl or aryl, and $R_4$ is hydrogen, alkyl, cycloalkyl, aralkyl, aryl or alkoxy.

3. A process according to claim 2, wherein there are prepared, from a compound of the formula II, a compound of the formula I in which $R_1$ is hydrogen or chlorine, $R_2$ is hydrogen, alkyl having 1 to 5 carbon atoms, alkoxy having 1 to 4 carbon atoms or chlorine, $R_3$ is hydrogen, alkyl having 1 to 12 carbon atoms, cycloalkyl having 5 to 8 carbon atoms or aralkyl having 7 to 9 carbon atoms, and $R_4$ is hydrogen, alkyl having 1 to 12 carbon atoms, cycloalkyl having 5 to 8 carbon atoms, aralkyl having 7 to 9 carbon atoms, phenyl or alkoxy having 1 to 12 carbon atoms.

4. A process according to claim 1, wherein the alkali metal hydroxide or alkali metal is used in amounts of at least 1 mole equivalent relative to the substrate to be reduced.

5. A process according to claim 1, wherein the alcohol is isopropanol or sec.-butanol.

6. A process according to claim 1, wherein the catalyst is an unsubstituted or substituted benzodiol or an unsubstituted or substituted naphthoquinone.

7. A process according to claim 1, wherein the reduction is carried out in a medium which contains at most 15% by volume of water, if any.

8. A process according to claim 1 wherein the strongly basic medium is produced by adding an alkali metal hydroxide or alkali metal.

* * * * *